United States Patent [19]

Bornstein

[11] Patent Number: 4,628,911
[45] Date of Patent: Dec. 16, 1986

[54] ARM SUSPENSION MITT

[76] Inventor: Jerome L. Bornstein, Suite 131, Encino, Calif. 91316

[21] Appl. No.: 724,023

[22] Filed: Apr. 17, 1985

[51] Int. Cl.⁴ .................. A61F 5/40; A61F 13/10; A61F 5/37; A61B 17/56
[52] U.S. Cl. .................. 128/77; 128/DIG. 20; 128/133
[58] Field of Search .................. 128/77, DIG. 20, 133

[56] References Cited

U.S. PATENT DOCUMENTS 3,198,197 8/1965 Van Halanger .................. 128/77
4,173,218 11/1979 Cronin .................. 128/DIG. 20
4,281,647 8/1981 Antypas .................. 128/77

Primary Examiner—Edgar S. Burr
Assistant Examiner—Tonya Eckstine
Attorney, Agent, or Firm—McAulay, Fields, Fisher, Goldstein & Nissen

[57] ABSTRACT

An arm suspension mitt immobilizes and positions a patient's arm for shoulder arthroscopy. The mitt includes outer and inner flexible portions which together define a package having an open end adapted to removably receive a hand inserted into a space radially inward of the inner flexible portion. An inflatable chamber is provided between the outer and inner portions. The inflatable chamber is sealed from the ambient atmosphere. A valve is provided in communication with the inflatable chamber for inflating same thus causing the inner flexible portion to collapse in a direction away from the outer flexible portion so as to conform the inner flexible portion around a hand within the space.

9 Claims, 5 Drawing Figures

ARM SUSPENSION MITT

BACKGROUND OF THE INVENTION

This invention relates to a device for immobilizing and suspending an arm during arthroscopy.

Arthroscopy is a recently developed and widely used diagnostic and surgical procedure which allows a physician to see inside of joints such as the knee, shoulder and ankle. The procedure involves the use of an arthroscope, a long thin, illuminated viewing scope with optical fibers on its tip, which is inserted through a very small incision into the joint. With the arthroscope a physician can quickly and easily assess joint damage by direct viewing, plan an appropriate repair operation and trim away damaged tissue using tiny instruments inserted through the arthroscope. The development of arthroscopy has reduced the cost of rehabiliative surgery and further has vastly reduced the time it takes to recuperate from such surgery.

When shoulder arthroscopy is performed it is necessary to immobilize and suspend the patient's arm. This is done by positioning the patient on his side with the shoulder to be examined uppermost. The arm should be at an angle of between 30° to 45° from the horizontal (abduction angle) and the shoulder itself should be bent to achieve about 15° flexion. This positioning maximizes the physician's access to the shoulder so that the joint can be most effectively viewed and repaired. Further, this positioning avoids over stretching of the brachial plexus during arthroscopy.

In order to obtain the necessary abduction and flexion angles for shoulder arthroscopy, it is necessary to secure the patient's hand and/or wrist at a position above and away from his body. This has heretofore been accomplished by securing the hand or wrist to a pole or other stable means using tape, rope, hard plastic devices, etc. Although these aforementioned devices secure the hand and places the arm and shoulder in proper position for the arthroscopy they are time consuming to set-up, not easy to keep sterile, and cause unnecessary discomfort and pressure on the patient's hand and arm. Further, visualization of the patient's hand and forearm is hampered due to the tape or rope, etc., thus making it difficult to monitor peripheral circulatory and other problems. As such, the aforementioned effects of taping and tying etc. are undesirable in any invasive medical procedure and are even less desirable in arthroscopy which is intended as a fairly quick, uncomplicated procedure which attempts to minimize soft tissue injuries and other complications.

Accordingly, it is a purpose of this invention to provide a device which can be used to hold a person's hand above and away from his body so as to properly position the person's arm and shoulder for arthroscopy.

Another object of this invention is to provide such a device which is relatively comfortable for the patient, easy to use, easy to keep sterile, which does not hamper visualization of the arm and hand, and which does not unduly press against or bind the patient's limb.

BRIEF DESCRIPTION

In brief, one embodiment of the invention involves an arm suspension mitt which is see-through and inflatable. The mitt includes an outer flexible portion and an inner flexible portion. The outer and inner flexible portions are substantially the same size and shape and together they define a package having an open end through which a person's hand can be removably inserted into a space inward of the inner flexible portion.

An inflatable chamber is defined by the inner and outer flexible portions of the mitt. The inflatable chamber is sealed from the ambient air. A valve on the outer flexible portion is in communication with the inflatable chamber. The valve is used to inflate the inflatable chamber. When the chamber is inflated, it causes the inner flexible portion to collapse in a direction away from the outer flexible portion. When the inner flexible portion is thus collapsed it will conform around a hand which is within the inward space. The hand can thus be held within the mitt without undue pressure and binding.

The mitt of this invention includes a panel with holes at an edge opposite the open end to allow the mitt with a hand held therein to be easily and quickly attached to a pole or other device so that the hand can be suspended over and away from the patient's body. The mitt can be quickly and easily covered with a disposable sterile cover.

DESCRIPTION OF THE PREFERRED EMBODIMENTS

Figure 1:
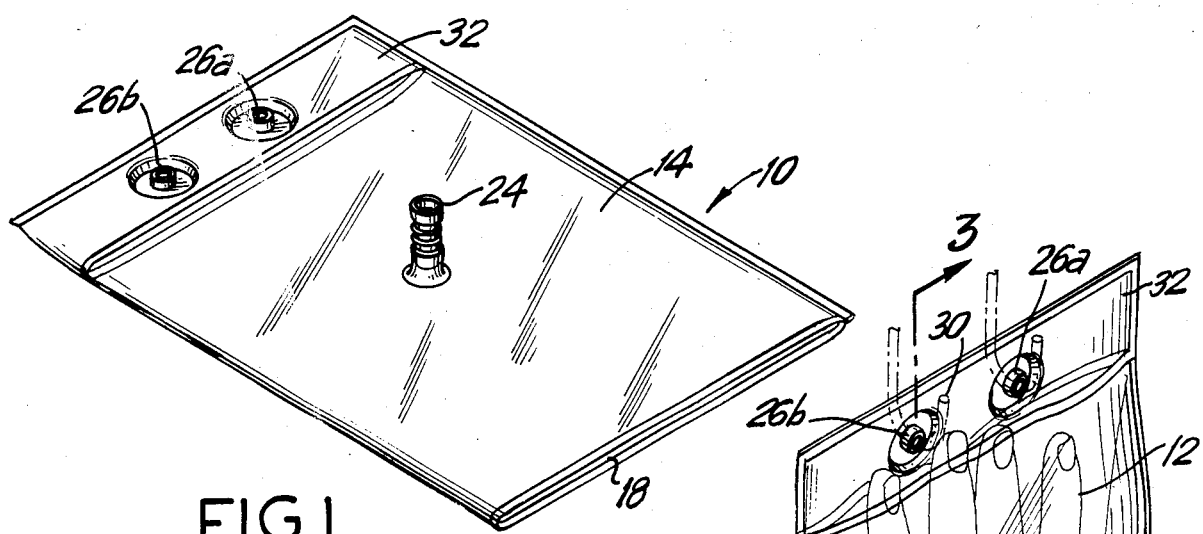
FIG. 1 is a perspective view of one embodiment of the arm mitt of the present invention, showing the mitt with the inflatable chamber not inflated.
Figure 2:
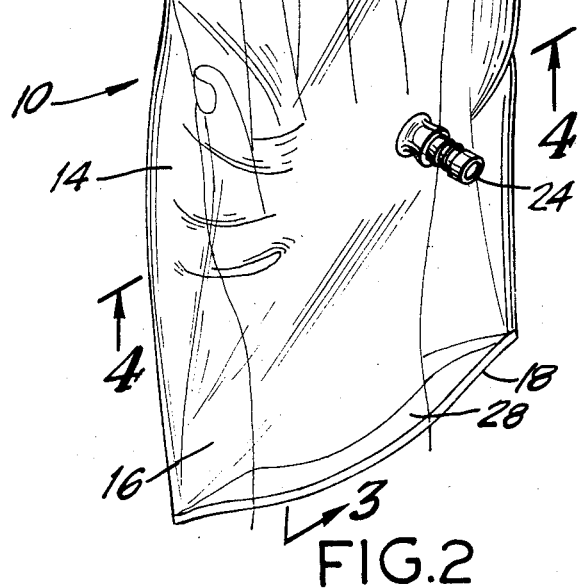
FIG. 2 is a perspective view of the arm mitt of the present invention, showing the inflatable chamber inflated with a hand held within the hand receiving area.

Referring to the drawings, the reference numeral 10 denotes the arm suspension mitt of the present invention. Mitt 10, as shown in FIGS. 2-5, is capable of retaining a hand 12 therein. As best seen in FIGS. 2 and 5, mitt 10 is see-through so that hand 12 can be easily observed when within the mitt.

Mitt 10 includes an outer flexible portion 14 and an inner flexible portion 16. Inner flexible portion 16 is collapsable. Outer flexible portion 14 and inner flexible portion 16 are of substantially the same size and shape and together define a mitt with an open end 18. Hand 12, can be removably inserted through open end 18 into a space 20, best seen in FIG. 3, which is situated radially inward of the inner flexible portion 16.

Figure 3:
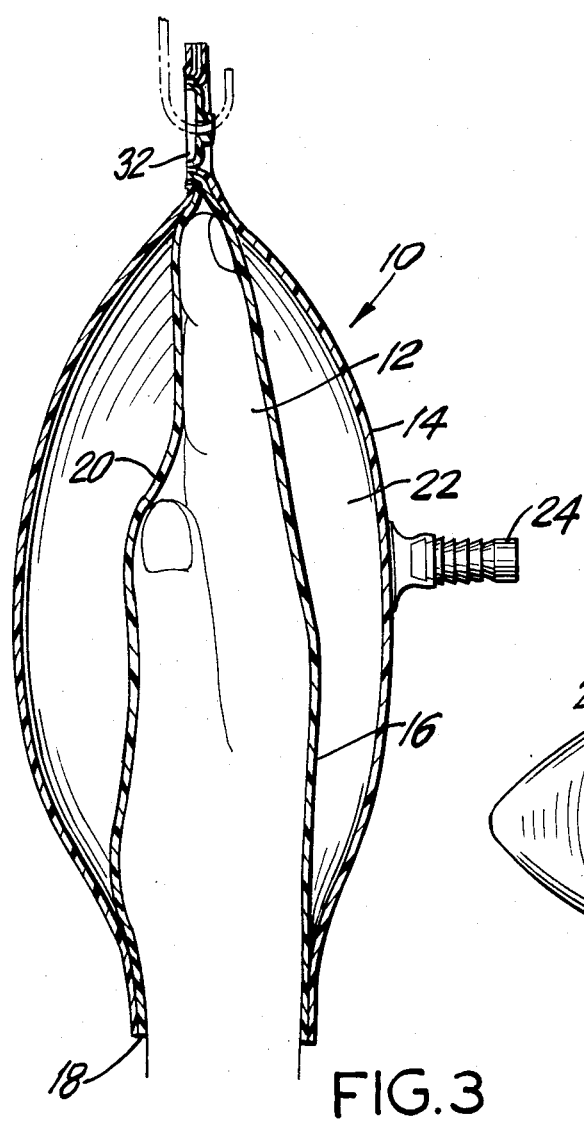
FIG. 3 is a sectional view taken generally along line 3—3 of FIG. 2.
Figure 4:
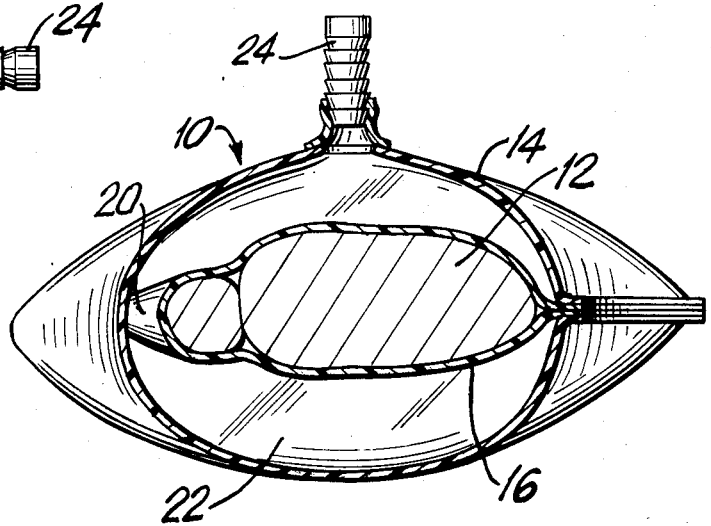
FIG. 4 is a sectional view taken generally along line 4—4 of FIG. 2.
Figure 5:
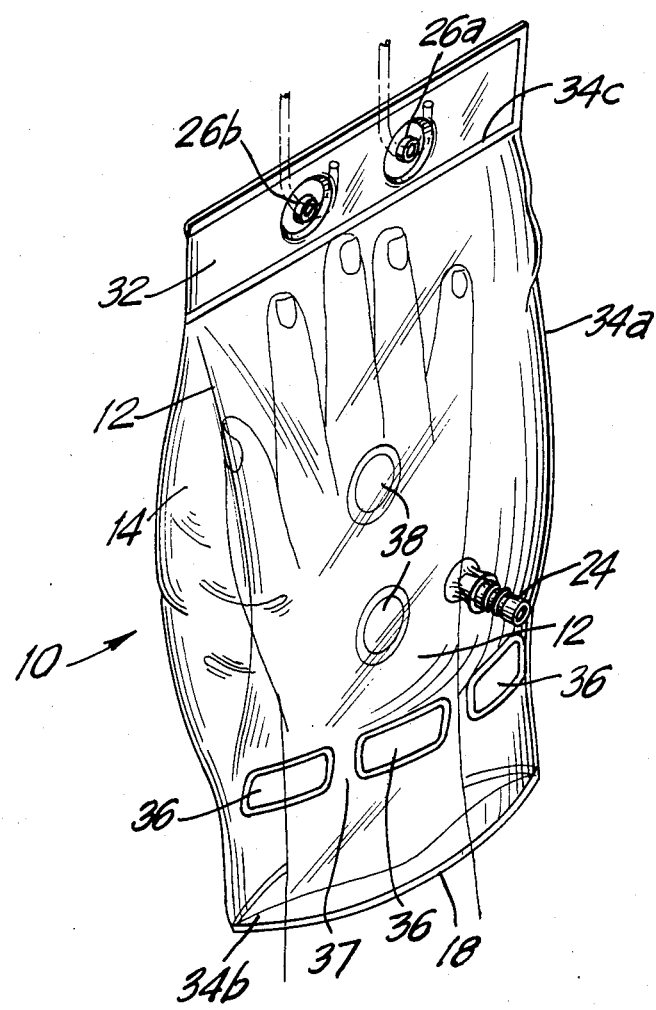
FIG. 5 is a view, analogous to FIG. 1 but showing another embodiment of the arm mitt of the present invention.

Mitt 10 includes an inflatable chamber 22, best seen in FIGS. 3 and 4, which is sealed from the ambient atmosphere. A valve 24, or other appropriate inflation means, is provided which is in communication with flexible chamber 22 and usable to inflate chamber 22. When chamber 22 is inflated it causes inner flexible portion 16 to collapse in a direction away from outer flexible portion 14 so as to conform inner flexible portion 16 around hand 12 held within space 20.

Mitt 10 can be made of any appropriate material, and one embodiment of this invention is made of a clear polyvinyl material. Mitt 10 includes a panel 32 having apertures 26a, 26b, or other appropriate means to receive hooks. The apertures 26a and 26b are positioned on the mitt opposite open end 18. Thus, when a hand is in the mitt, open end 18 is proximate the wrist 28 while the apertures 26a and 26b are proximate the fingertips 30. Panel 32 is made of a polyvinyl material and is heat sealed to the main portion of mitt 10. As shown in FIG. 2 the heat seal may be such that the fingertips 30 extend into the panel 32, or, as shown in FIG. 5, the heat seal may be such that the fingertips cannot extend into panel 32.

In one embodiment of mitt 10, as shown in FIG. 5, inner portion 16 and outer portion 14 are connected to one another along only three edges 34a, 34b and 34c. Although the inner and outer portions may be connected to one another along four edges, as shown in FIG. 2, this is not necessary and is a more expensive way of manufacturing the mitt.

As shown in FIG. 5, spaced apart, heat sealed rectangles 36 can be included on both faces of outer portion 14. The heat sealed rectangles are spaced from and above the open end 18 and serve to form air-channels which create a narrowed cuff area 37 which helps mitt 10 conform to a human wrist, when the inflatable chamber 22 is inflated. A plurality of spaced apart non-slip vinyl foam patches 38 can be affixed to each inner face of inner portion 16 to help retain hand 12 within the mitt 10.

What is claimed:

1. An arm suspension mitt usable during surgical procedures having means to enable continuous monitoring of blood circulation in the fingers, said means comprising:
    an outer flexible portion;
    an inner flexible portion, said outer and inner portions together defining a package having an open end for removably receiving a hand inserted into a space radially inward of said inner flexible portion, said inner flexible portion being undivided to provide space around each finger and between each finger to avoid constriction of the blood vessels of the fingers;
    an inflatable chamber between said inner portion and said outer flexible portion, said inflatable chamber being sealed from the ambient atmosphere;
    valve means in communication with said inflatable chamber for inflating said inflatable chamber to thus cause said inner flexible portion to collapse in a direction away from said outer flexible portion so as to conform said inner flexible portion around said hand within said space;
    said mitt being see-through to permit visualization of the hand received therein.

2. The mitt of claim 1 wherein said inner portion is collapsible.

3. The mitt of claim 1 wherein said inner and outer portions are connected to one another along at least one edge.

4. The mitt of claim 1 wherein said inner and outer portions are connected to one another along three edges.

5. The mitt of claim 1 wherein said mitt is made of a clear polyvinyl material.

6. The mitt of claim 1 further comprising hook receiving means positioned at an edge opposite said open end.

7. The mitt of claim 1 further comprising cuff forming means spaced from and above said open end for permitting said mitt to more closely conform to a wrist when said inflatable chamber is inflated.

8. The mitt of claim 1 further comprising at least one non-slip patch connected to each inner face of said inner portion to aid in retaining a hand in said space when said inflatable chamber is inflated.

9. An arm suspension mitt for use during arthroscopy, said mitt capable of holding and suspending a person's hand above and away from the person's body, having means to enable continuous monitoring of blood circulation in the fingers, said means comprising:
    a flexible, see-through double walled package having an open bottom, said double walled package having a radially outboard wall and a radially inboard wall, said walls being substantially the same size and shape and being connected to one another along three edges;
    an inflatable chamber between said outboard wall and said inboard wall, said inflatable chamber being sealed from the ambient atmosphere; and
    a hand receiving area radially inward of said inboard wall to removably receive a hand which is inserted through said package open bottom, said hand receiving area being undivided to provide space around each finger and between each finger to avoid constriction of the blood vessels of the fingers;
    valve means on said outboard wall and in communication with said inflatable chamber;
    said inflatable chamber having a deflated state during which said hand can be inserted and removed from said hand receiving area and an inflated state during which said hand is securely held in said hand receiving area by said radially inboard wall which is collapsed in a direction away from said outboard wall in response to inflation of said chamber.

* * * * *